US008604064B2

(12) United States Patent
Kohl et al.

(10) Patent No.: US 8,604,064 B2
(45) Date of Patent: *Dec. 10, 2013

(54) PROCESS FOR THE PREPARATION OF ROFLUMILAST

(71) Applicant: Takeda GmbH, Constance (DE)

(72) Inventors: Bernhard Kohl, Constance (DE); Bernd Mueller, Constance (DE); Walter Palosch, Rielasingen (DE)

(73) Assignee: Takeda GmbH, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/860,248

(22) Filed: Apr. 10, 2013

(65) Prior Publication Data

US 2013/0224299 A1    Aug. 29, 2013

Related U.S. Application Data

(63) Continuation of application No. 13/547,945, filed on Jul. 12, 2012, which is a continuation of application No. 12/292,795, filed on Nov. 26, 2008, now abandoned, which is a continuation of application No. 10/531,720, filed as application No. PCT/EP2004/050272 on Mar. 8, 2004, now Pat. No. 7,470,791.

(30) Foreign Application Priority Data

Mar. 10, 2003  (EP) .................................. 03005245

(51) Int. Cl.
*A61K 31/44* (2006.01)

(52) U.S. Cl.
USPC ........................................................ 514/352

(58) Field of Classification Search
USPC ........................................................ 514/352
See application file for complete search history.

(56) References Cited

U.S. PATENT DOCUMENTS

| | | |
|---|---|---|
| 3,065,142 A | 11/1962 | Antonides |
| 4,006,227 A | 2/1977 | Gallegos et al. |
| 4,024,240 A | 5/1977 | Thakkar |
| 4,343,804 A | 8/1982 | Munson et al. |
| 4,349,563 A | 9/1982 | Gilbert et al. |
| 4,450,164 A | 5/1984 | Bristol et al. |
| 4,464,372 A | 8/1984 | Bristol et al. |
| 4,563,455 A | 1/1986 | Ueda et al. |
| 4,621,084 A | 11/1986 | Takaya et al. |
| 4,686,227 A | 8/1987 | Ueda et al. |
| 4,725,601 A | 2/1988 | Ueda et al. |
| 4,753,945 A | 6/1988 | Gilbard et al. |
| 4,769,384 A | 9/1988 | Kise et al. |
| 4,782,055 A | 11/1988 | Ueda et al. |
| 4,791,117 A | 12/1988 | Press |
| 4,806,550 A | 2/1989 | Ife et al. |
| 4,831,041 A | 5/1989 | Shiokawa et al. |
| 4,833,149 A | 5/1989 | Press |
| 4,839,353 A | 6/1989 | Hosoi et al. |
| 4,900,775 A | 2/1990 | Smith et al. |
| 4,920,129 A | 4/1990 | Shiokawa et al. |
| 5,006,595 A | 4/1991 | Smith et al. |
| 5,011,843 A | 4/1991 | Shell |
| 5,041,442 A | 8/1991 | Romero et al. |
| 5,051,508 A | 9/1991 | Brown et al. |
| 5,089,504 A | 2/1992 | Ife et al. |
| 5,102,892 A | 4/1992 | Geiss et al. |
| 5,112,834 A | 5/1992 | Senn-Bilfinger |
| 5,188,838 A | 2/1993 | Deleuil et al. |
| 5,200,417 A | 4/1993 | Brown et al. |
| 5,215,999 A | 6/1993 | Uchida et al. |
| 5,252,580 A | 10/1993 | Takahashi et al. |
| 5,262,171 A | 11/1993 | Login et al. |
| 5,286,494 A | 2/1994 | Fechner et al. |
| 5,320,848 A | 6/1994 | Geyer et al. |
| 5,326,879 A | 7/1994 | Takahashi et al. |
| 5,340,827 A | 8/1994 | Beeley et al. |
| 5,380,532 A | 1/1995 | Deleuil et al. |
| 5,409,943 A | 4/1995 | Ife et al. |
| 5,429,824 A | 7/1995 | June |
| 5,439,917 A | 8/1995 | Briving et al. |
| 5,534,515 A | 7/1996 | Grundler |
| 5,665,730 A | 9/1997 | Senn-Bilfinger et al. |
| 5,677,302 A | 10/1997 | Karimian et al. |
| 5,686,458 A | 11/1997 | Lee et al. |
| 5,698,711 A | 12/1997 | Palfreyman |
| 5,712,298 A | 1/1998 | Amschler |
| 5,719,161 A | 2/1998 | Rainer |

(Continued)

FOREIGN PATENT DOCUMENTS

| | | |
|---|---|---|
| CA | 2016141 | 11/1990 |
| CA | 2497176 | 3/2004 |

(Continued)

OTHER PUBLICATIONS

Antoni et al., "Synthesis of [18F] Labelled Roflumilast Using Difluoro [18F] Bromomethane as Alkylating Agent," *Synthesis and Applications of Isotopically Labeled Compounds*, 2000, 7:375-376.

(Continued)

*Primary Examiner* — Samantha Shterengarts
(74) *Attorney, Agent, or Firm* — Fish & Richardson P.C.

(57) ABSTRACT

A method for the treatment of chronic obstructive pulmonary disease (COPD), including administering to a patient suffering from COPD, a therapeutically effective amount of roflumilast having a purity of greater than or equal to 99% by weight, and N-(3,5-dichloropyrid-4-yl)-3-cyclopropyl-methoxy-4-hydroxybenzamide present (relative to roflumilast) in an amount greater than zero and less than 0.1% by weight.

23 Claims, No Drawings

(56) References Cited

U.S. PATENT DOCUMENTS

| | | |
|---|---|---|
| 5,762,953 A | 6/1998 | Venkateshwaran |
| 5,824,687 A | 10/1998 | Senn-Bilfinger |
| 5,891,904 A | 4/1999 | Stief et al. |
| 5,972,381 A | 10/1999 | Sangekar et al. |
| 5,972,927 A | 10/1999 | Pascal et al. |
| 6,114,537 A | 9/2000 | Karimian et al. |
| 6,124,313 A | 9/2000 | Grundler et al. |
| 6,132,770 A | 10/2000 | Lundberg |
| 6,160,119 A | 12/2000 | Senn-Bilfinger |
| 6,174,878 B1 | 1/2001 | Gamache et al. |
| 6,218,400 B1 | 4/2001 | Daugan et al. |
| 6,231,885 B1 | 5/2001 | Carrara |
| 6,255,326 B1 | 7/2001 | Amschler |
| 6,258,833 B1 | 7/2001 | Martins et al. |
| 6,265,415 B1 | 7/2001 | Amin et al. |
| 6,270,807 B1 | 8/2001 | Danielson et al. |
| 6,288,118 B1 | 9/2001 | Nieman et al. |
| 6,313,136 B1 | 11/2001 | Amin et al. |
| 6,313,137 B1 | 11/2001 | Amin et al. |
| 6,328,993 B1 | 12/2001 | Linder et al. |
| 6,348,602 B1 | 2/2002 | Fowler et al. |
| 6,375,968 B1 | 4/2002 | Quong |
| 6,379,682 B1 | 4/2002 | Tchinnis et al. |
| 6,383,510 B1 | 5/2002 | Linder et al. |
| 6,384,048 B1 | 5/2002 | Senn-Bilfinger |
| 6,417,190 B1 | 7/2002 | Hoffmann et al. |
| 6,432,451 B1 | 8/2002 | Lee et al. |
| 6,436,953 B1 | 8/2002 | Senn-Bilfinger |
| 6,436,970 B1 | 8/2002 | Hafner et al. |
| 6,448,274 B2 | 9/2002 | Friesen et al. |
| 6,498,173 B1 | 12/2002 | Kilian |
| 6,503,923 B1 | 1/2003 | Senn-Bilfinger |
| 6,531,493 B1 | 3/2003 | Kley et al. |
| 6,537,983 B1 | 3/2003 | Biggadike et al. |
| 6,555,583 B2 | 4/2003 | Nieman et al. |
| 6,579,884 B1 | 6/2003 | Amin et al. |
| 6,613,775 B1 | 9/2003 | Amin et al. |
| 6,624,181 B1 | 9/2003 | Killian et al. |
| 6,630,161 B1 | 10/2003 | Leesman |
| 6,670,394 B1 | 12/2003 | Christensen et al. |
| 6,677,362 B1 | 1/2004 | Ghebre et al. |
| 6,743,443 B1 | 6/2004 | Furitsu et al. |
| 6,767,557 B2 | 7/2004 | Ulrich et al. |
| 6,822,114 B1 | 11/2004 | Williams et al. |
| 6,872,382 B1 | 3/2005 | Gamache et al. |
| 6,897,229 B2 | 5/2005 | Kilian |
| 7,056,936 B2 | 6/2006 | Killian et al. |
| 7,147,869 B2 | 12/2006 | Dietrich et al. |
| 7,175,854 B2 | 2/2007 | Dietrich et al. |
| 7,182,958 B1 | 2/2007 | Oren et al. |
| 7,357,943 B2 | 4/2008 | Linder et al. |
| 7,393,860 B1 | 7/2008 | Sen-Bilfinger |
| D580,547 S | 11/2008 | Lolis et al. |
| 7,745,646 B2 | 6/2010 | Govek et al. |
| 7,785,630 B2 | 8/2010 | Dietrich et al. |
| 7,790,198 B2 | 9/2010 | Dietrich et al. |
| 7,794,752 B1 | 9/2010 | Dietrich et al. |
| 7,927,623 B2 | 4/2011 | Sugimoto et al. |
| 7,951,397 B2 | 5/2011 | Dietrich et al. |
| 7,951,398 B2 | 5/2011 | Dietrich et al. |
| 2001/0044409 A1 | 11/2001 | Ghebre et al. |
| 2002/0002191 A1 | 1/2002 | Friesen |
| 2002/0006418 A1 | 1/2002 | Kung et al. |
| 2002/0086039 A1 | 7/2002 | Lee et al. |
| 2002/0193393 A1 | 12/2002 | Pairet et al. |
| 2003/0018071 A1 | 1/2003 | Rennard et al. |
| 2003/0092706 A1 | 5/2003 | Barsig |
| 2003/0099700 A1 | 5/2003 | Faham et al. |
| 2003/0195233 A1 | 10/2003 | Magee |
| 2003/0207845 A1 | 11/2003 | Keating et al. |
| 2003/0212112 A1 | 11/2003 | Murdoch et al. |
| 2004/0024007 A1 | 2/2004 | Pairet et al. |
| 2004/0058896 A1 | 3/2004 | Dietrich et al. |
| 2004/0058950 A1 | 3/2004 | Meade et al. |
| 2004/0101558 A1 | 5/2004 | Dietrich et al. |
| 2004/0151722 A1 | 8/2004 | Banerjee et al. |
| 2004/0241235 A1 | 12/2004 | Lebon et al. |
| 2005/0159492 A1 | 7/2005 | Dietrich et al. |
| 2006/0035872 A1 | 2/2006 | Villa et al. |
| 2006/0069155 A1 | 3/2006 | Edelson |
| 2006/0084684 A1 | 4/2006 | Bolle et al. |
| 2006/0084685 A1 | 4/2006 | Koenen et al. |
| 2006/0105038 A1 | 5/2006 | Lai et al. |
| 2006/0142308 A1 | 6/2006 | Kolassa et al. |
| 2006/0147382 A1 | 7/2006 | Bundschuh et al. |
| 2006/0159758 A1 | 7/2006 | Gandhi et al. |
| 2006/0198889 A1 | 9/2006 | Sandhu et al. |
| 2006/0199865 A1 | 9/2006 | Beume et al. |
| 2006/0228410 A1 | 10/2006 | Dumont et al. |
| 2006/0269600 A1 | 11/2006 | Dietrich |
| 2007/0122474 A1 | 5/2007 | Dietrich |
| 2007/0134729 A1 | 6/2007 | Christensen et al. |
| 2007/0254928 A1 | 11/2007 | Wollin et al. |
| 2008/0193544 A1 | 8/2008 | Bruck-Scheffler et al. |
| 2008/0280958 A1 | 11/2008 | Bolle et al. |
| 2010/0310477 A1 | 12/2010 | Pairet et al. |
| 2011/0060016 A1 | 3/2011 | Dietrich et al. |
| 2011/0212182 A1 | 9/2011 | Lebon et al. |
| 2011/0251244 A1 | 10/2011 | Dietrich et al. |
| 2011/0313005 A1 | 12/2011 | Bolle et al. |

FOREIGN PATENT DOCUMENTS

| | | |
|---|---|---|
| CN | 1126468 | 11/2003 |
| CN | 1189832 | 2/2005 |
| DE | 3011490 | 3/1981 |
| DE | 3622036 | 1/1987 |
| DE | 3917232 | 11/1990 |
| DE | 3943385 | 7/1991 |
| DE | 69101493 | 8/1994 |
| DE | 10061137 | 6/2002 |
| DE | 19925710 | 10/2002 |
| EP | 33094 | 8/1981 |
| EP | 68378 | 1/1983 |
| EP | 120589 | 10/1984 |
| EP | 125756 | 11/1984 |
| EP | 165545 | 12/1985 |
| EP | 228006 | 7/1987 |
| EP | 261912 | 3/1988 |
| EP | 264883 | 4/1988 |
| EP | 266890 | 5/1988 |
| EP | 268989 | 6/1988 |
| EP | 308917 | 3/1989 |
| EP | 163965 | 11/1989 |
| EP | 368158 | 5/1990 |
| EP | 120352 | 6/1990 |
| EP | 438359 | 7/1991 |
| EP | 399267 | 12/1991 |
| EP | 204285 | 1/1992 |
| EP | 259174 | 3/1992 |
| EP | 307078 | 8/1992 |
| EP | 509974 | 10/1992 |
| EP | 510562 | 10/1992 |
| EP | 330485 | 5/1993 |
| EP | 563024 | 9/1993 |
| EP | 387821 | 8/1994 |
| EP | 393926 | 9/1994 |
| EP | 617612 | 10/1994 |
| EP | 537532 | 11/1996 |
| EP | 535529 | 7/1997 |
| EP | 1118615 | 7/2001 |
| EP | 1161950 | 12/2001 |
| EP | 1187601 | 3/2002 |
| EP | 1105390 | 6/2003 |
| EP | 1199074 | 4/2004 |
| EP | 1366760 | 9/2005 |
| EP | 1120120 | 4/2009 |
| EP | 1478399 | 3/2012 |
| ES | 2176252 | 12/2002 |
| JP | 61205208 | 9/1986 |
| JP | 2270873 | 11/1990 |
| JP | 2049720 | 12/1990 |
| JP | 3031280 | 12/1991 |
| JP | 3284622 | 12/1991 |

(56) References Cited

FOREIGN PATENT DOCUMENTS

| | | |
|---|---|---|
| JP | 3284686 | 12/1991 |
| JP | 4212359 | 8/1992 |
| JP | 5271070 | 10/1993 |
| JP | 8-512041 | 12/1996 |
| JP | 9059152 | 3/1997 |
| JP | 11152224 | 6/1999 |
| JP | 2000516633 | 12/2000 |
| JP | 20086502 | 7/2009 |
| JP | 2009167052 | 7/2009 |
| KR | 2000-0029011 | 5/2000 |
| NO | 20032593 | 8/2003 |
| PL | 178314 | 1/1995 |
| WO | 8900570 | 1/1989 |
| WO | 8908127 | 9/1989 |
| WO | 9114677 | 10/1991 |
| WO | 9117164 | 11/1991 |
| WO | 9118887 | 12/1991 |
| WO | 9206979 | 4/1992 |
| WO | 9212961 | 8/1992 |
| WO | 9212969 | 8/1992 |
| WO | 9221328 | 12/1992 |
| WO | 9308190 | 4/1993 |
| WO | 9312090 | 6/1993 |
| WO | 9315055 | 8/1993 |
| WO | 9315056 | 8/1993 |
| WO | 9315071 | 8/1993 |
| WO | 93/25517 | 12/1993 |
| WO | 94/02465 | 2/1994 |
| WO | 9414795 | 7/1994 |
| WO | 9424130 | 10/1994 |
| WO | 95/01338 | 1/1995 |
| WO | 9527714 | 10/1995 |
| WO | 9617830 | 6/1996 |
| WO | 9725030 | 7/1997 |
| WO | 9736905 | 10/1997 |
| WO | 9807400 | 2/1998 |
| WO | 9820858 | 5/1998 |
| WO | 9835683 | 8/1998 |
| WO | 9837080 | 8/1998 |
| WO | 9842707 | 10/1998 |
| WO | 9854188 | 12/1998 |
| WO | 9929299 | 6/1999 |
| WO | 9955705 | 11/1999 |
| WO | 9955706 | 11/1999 |
| WO | 9963940 | 12/1999 |
| WO | 0010999 | 3/2000 |
| WO | 0012501 | 3/2000 |
| WO | 0017200 | 3/2000 |
| WO | 0018388 | 4/2000 |
| WO | 0026217 | 5/2000 |
| WO | 0011000 | 6/2000 |
| WO | 0050011 | 8/2000 |
| WO | 00/51598 | 9/2000 |
| WO | 0035428 | 9/2000 |
| WO | 0053182 | 9/2000 |
| WO | 0063211 | 10/2000 |
| WO | 0066123 | 11/2000 |
| WO | 0074654 | 12/2000 |
| WO | 0108686 | 2/2001 |
| WO | 0132165 | 5/2001 |
| WO | 0146136 | 6/2001 |
| WO | 0157025 | 8/2001 |
| WO | 0160358 | 8/2001 |
| WO | 01/90076 | 11/2001 |
| WO | 0115678 | 1/2002 |
| WO | 02/09689 | 2/2002 |
| WO | 0238155 | 5/2002 |
| WO | 0245693 | 6/2002 |
| WO | 02072072 | 12/2002 |
| WO | 03039552 | 5/2003 |
| WO | 03/070279 | 8/2003 |
| WO | 03097050 | 11/2003 |
| WO | 03/099334 | 12/2003 |
| WO | 03099278 | 12/2003 |
| WO | 03105902 | 12/2003 |
| WO | 2004017974 | 3/2004 |
| WO | 2004019944 | 3/2004 |
| WO | 2004/033430 | 4/2004 |
| WO | 2004052345 | 6/2004 |
| WO | 2004066974 | 8/2004 |
| WO | 2004080967 | 9/2004 |
| WO | 2004103407 | 12/2004 |
| WO | 2005011602 | 2/2005 |
| WO | 2005013944 | 2/2005 |
| WO | 2005/026095 | 3/2005 |
| WO | 2005020961 | 3/2005 |
| WO | 2005034871 | 4/2005 |
| WO | 2005041864 | 5/2005 |
| WO | 2006097456 | 9/2006 |
| WO | 2008006050 | 1/2008 |

OTHER PUBLICATIONS

Bundschuh et al., "In vivo eficacy in airway disease models of roflumilast, a novel orally active PDE4 inhibitory," *J. Pharmacol. Exp. Thera.*, 2000, 297(1):280-290.

Cook et al., "Process Development o the PDE IV Inhibitor 3-(Cyclopentyloxy)-*N*-(3,5-dichloropyrid-4-yl)-4-methoxybenzamide," *Organic Process Research & Development*, 1998, 2:157-168.

Hatzelmann et al., Anti-Inflammatory and immunomodulatory potential of the novel PDE4 inhibitor roflumilast in vitro, *J. Pharm. Exp. Thera.*, 2000, 297(1):267-279.

Hauns et al., Four week treatment with the new PDE4 inhibitor roflumilast in patients with exercise-induced asthma: safety, efficacy and inhibition of the TNF-a -ex vivo, Eur Respir J., 2000, 16 (Suppl 31):A3805.

Pleiss et al., "Synthesis of [18F] Labelled Roflumilast using difluoro [18F] bromomethane as alkylating agent," *Synth. Appl. Isotop. Lab. Comp.*, 2000, 7:375-376.

Reid, *Current Opinion in Investig. Drugs*, 2002, 3(8):1165-1170.

Barnes, "Emerging pharmacotherapies for COPD," *Chest*, 2008, 134: 1278-86.

Bateman et al., "Efficacy of roflumilast in patients with a history of frequent exacerbations: pooled data from pivotal 12-month studies," Poster , ERS Barcelona Sep. 2010, 1 page.

Boehmer et al., "Effects of the Dual Pathway Inhibitor Cimetidine on the Pharmacokinetics of Roflumilast and Roflumilast N-oxide," VKliPha 2007 Poster, 2007, 1 page.

Boswell et al., "Are phosphodiesterase 4 inhibitors just more theophylline?," *J Allergy Clin Immuno*, 1 2006, 117: 1237-43.

Burge et al., "Randomised, double blind, placebo controlled study of fluticasone propionate in patients with moderate to severe chronic obstructive pulmonary disease: the ISOLDE trial," *BMJ*, 2000, 320: 1297-1303

Calverley et al., "Defining patient populations in COPD: experience with roflumilast," COPD7 Birmingham, 2010, 1 page.

Calverley et al., "Effect of roflumilast on lung function," ATS 2006 Presentation, 12 pages.

Calverley et al., "Roflumilast in symptomatic chronic obstructive pulmonary disease: two randomized clinical trials," *Lancet*, 2009, 374: 685-94, Supplementary Web Appendix Content.

Calverley et al., "Roflumilast in symptomatic chronic obstructive pulmonary disease: two randomized clinical trials," *Lancet*, 2009, 374:685-94.

Celli and MacNee, "Standards for the diagnosis and treatment of patients with COPD: A summary of the ATS/ERS position paper," *Eur Respir J*, 2004, 23: 932-46.

Chen at al., "Long-acting bronchodilator therapy for the treatment of chronic obstructive pulmonary disease," *Ann Pharmacother*, 2008, 42: 1832-42.

deMey et al., "Repeated-dose Co-administration of Roflumilast and Formoterol Does not Alter the Pharmacokinetics of Either Drug," ATS 2006 Poster, 2006, 1 page.

deMey et al., "Roflumilast Does not Potentiate Tachycardia Associated with Formoterol," ATS 2006 Poster, 2006, 1 page.

Eakin et al., "Validation of a new dyspnea measure: The UCSD shortness of breath questionnaire," *Chest*, 1998, 113:619-24.

(56) References Cited

OTHER PUBLICATIONS

Engelstatter, "Roflumilast, an oral, once-daily phosphodiesterase 4 (PDE4) inhibitor, does not exhibit bronchodilatory activity," *Ann Allergy Asthma Immunol*, 2005, 94:169 (abstract).

Fabbri et al, "Effect of Roflumilast on Exacerbations: a 1-year Study in Patients with Severe to Very Severe COPD," ATS 2006 Poster, 2006, 1 page.

Fabbri et al., "Roflumilast in moderate-to-severe chronic obstructive pulmonary disease treated with longacting bronchodilators: two randomized clinical trials," 2009, Web Appendix, 28 pages.

Facius et al., "Modelling and simulation based techniques to support tiral design of roflumilast phase III trials," 2011, Athens Jun. 7-10, 2011, Poster, Modelling Simulation techniques Trial Design, Roflumilast, 1 page.

FDA PADAC Roflumilast, Questions and Answers presented UCM20871207, Apr. 2010, 27 pages.

Grootendorst et al., "Does a single dose of the phosphodiesterase 4 inhibitor, cilomilast (15 mg), induce bronchodilation in pateints with chronic obstructive pulmonary disease?," Pulmonary *Pharmacology and Therapeutics*, 2003, 16:115-120.

Keene et al., "Statistical analysis of COPD exacerbations," *Eur Respir J*, 2008, 32: 1421-22.

Keene et al., "Statistical analysis of exacerbation rates in COPD: Tristan and Isolde revisited," *Eur Respir J*, 2008, 32: 17-24.

Lahu et al., "Effects of steady-state enoxacin on single-dose pharmacokinetics of roflumilast and roflumilast N-oxide," ERS Sep. 2009 Poster, 2009, 1 page.

Lahu et al., "Modeling and simulation in successful drug development Programs: characterization of exacerbation reduction with roflumilast to corroborate the importance of defining patient subsets in COPD," ERS Sep. 2011 Modelling Simulation, 2011, 1 page.

Lahu et al., Effects of steady-state enoxacin on single-dose pharmacokinetics of roflumilast and roflumilast N-oxide. *J. Clin. Pharm.*, May 2010, 8 pages.

Lipworth, "Phosphodiesterase-4 inhibitors for asthma and chronic obstructive pulmonary desease," *Lancet*, 2005, 365:167-175.

Muise et al., "Comparison of inhibition of ovalbumin-induced bronchoconstriction in guinea pigs and in vitro inhibition of tumor necrosis factor-a formation with phosphodiesterase 4 (PDE4) selective inhibitors," *Biochem Pharmacol*, 2002 vol. 63 p. 1527-35.

Nassr et al., "Effects of CYP3A4 by Rifampicin on the Pharmacokinetics of roflumilast and roflumilast N-oxide," German pharmacology Meeting, Wurzburg, 2006, Poster, Rifampicin Roflumilast, 1 page.

O'Donnell et al., "Canadian thoracic society recommendations for management of chronic obstructive pulmonary disease- 2008 update-highlights for primary care," *Can Respir J*, 2008 vol. 15:Suppl A P, 1A-8A.

Quanjer et al., "Lung volumes and forced ventilatory flows," *Eur Respir J*, 1993, 6(suppl): 5-40.

Rabe et al., "Theophylline and selective PDE inhibitors as bronchodilators and smooth muscle relaxants," *Eur Respir J*, 1995, 8:637-42.

Roflumilast—Daliresp Full Prescribing Information, FDA, 2011, 14 pages.

Roflumilast—European Approval Documents Daxas, "Summary of Product Characteristics," Annex 1, 2010, 11 pages.

Roflumilast—European Approval Documents Daxas, Package Leaflet, "Information for the user-Daxas 500 micrograms film-coated tablets," 2010, 7 pages.

Sin and Man, "Systematic inflammation and mortality in chronic obstructive pulmonary disease," *Can J Phsiol Pharmacol* ,2007, 85:141-47.

Singh et al., "Long-term use of inhaled-corticosteroids and the risk of pneumonia in chronic obstructive pulmonary disease," *Arch Intern Med*, 2009, 169: 219-229.

Suissa et al., "Passive smoking and asthma death," *Eur Respir J*,2008, 32: 1117-18.

Szafranski et al., "Efficacy and safety of budesonide/formoterol in the management of chronic obstructive pulmonary disease," *Eur Respir J*, 2003, 21: 74-81.

USPTO Final Office Action issued in U.S. Appl. No. 10/505,138, dated Feb. 2, 2006, 10 pages.

USPTO Final Office Action issued in U.S. Appl. No. 10/505,138, dated May 30, 2007, 7 pages.

USPTO Final Office Action issued in U.S. Appl. No. 10/505,138, dated Oct. 16, 2008, 8 pages.

USPTO Final Office Action issued in U.S. Appl. No. 10/505,138, dated Nov. 12, 2008, 8 pages.

USPTO Final Office Action issued in U.S. Appl. No. 11/501,836, dated May 7, 2010, 13 pages.

USPTO Final Office Action issued in U.S. Appl. No. 11/501,836, dated Oct. 11, 2012, 73 pages.

USPTO Final Office Action issued in U.S. Appl. No. 12/876,996, dated Oct. 11, 2012, 58 pages.

USPTO Non-final Office Action issued in U.S. Appl. No. 10/505,138, dated Sep. 1, 2005, 9 pages.

USPTO Non-final Office Action issued in U.S. Appl. No. 10/505,138, dated Nov. 3, 2006, 16 pages.

USPTO Non-final Office Action issued in U.S. Appl. No. 10/505,138, dated Feb. 27, 2008, 15 pages.

USPTO Non-final Office Action issued in U.S. Appl. No. 11/501,836, dated Mar. 20, 2009, 7 pages.

USPTO Non-final Office Action issued in U.S. Appl. No. 11/501,836, dated Aug. 7, 2009, 12 pages.

USPTO Non-final Office Action issued in U.S. Appl. No. 11/501,836, dated Feb. 29, 2012, 9 pages.

USPTO Non-final Office Action issued in U.S. Appl. No. 12/876,996, dated Feb. 29, 2012, 15 pages.

USPTO Non-final Office Action issued in U.S. Appl. No. 13/008,842, Jan. 4, 2012, 12 pages.

USPTO Non-final Office Action issued in U.S. Appl. No. 10/531,720, dated Jan. 18, 2008, 7 pages.

USPTO Non-final Office Action issued in U.S. Appl. No. 12/292,795, dated Aug. 11, 2011, 10 pages.

USPTO Notice of Allowance issued in U.S. Appl. No. 10/505,138, dated Mar. 18, 2011, 55 pages.

USPTO Notice of Allowance issued in U.S. Appl. No. 13/008,842, dated Oct. 15, 2012, 44 pages.

USPTO Notice of Allowance issued in U.S. Appl. No. 13/008,842, dated Dec. 18, 2012, 4 pages.

USPTO Notice of Allowance issued in U.S. Appl. No. 13/008,842, dated Feb. 27, 2013, 12 pages.

USPTO Notice of Allowance issued in U.S. Appl. No. 10/531,720, dated Aug. 28, 2008, 6 pages.

USPTO Notice of Allowance issued in U.S. Appl. No. 12/292,795, dated Apr. 24, 2012, 7 pages.

USPTO Supplemental Notice of Allowability issued in U.S. Appl. No. 10/531,720, dated Nov. 7, 2008, 4 pages.

Wedzicha et al., "The prevention of chronic obstructive pulmonary disease exacerbations by salmeterol/fluticasone propionate or tiotropium bromide," *Am J Respir Crit Care Med*, 2008, 177:19-26.

ZuWallack et al., "Salmeterol plus theophylline combination therapy in the treatment of COPD," *Chest*, 2001, 119: 1661-70.

"Glossary", Ph Eur Monogra)2h, vol. 1502, p. 1-2, (2005).

"Remington: Practice of the Science and Pharmacy", Mack Publishing: Company: Easton, Pennsylvania, p. vii-viii and 1618-1629, (1995).

Academic book Applied Pharmacy Farmacja Stosowana Fiebig Janicki p. 267-268 2001.

Ammar et al., "Improvement of the biological performance of oral anticoagulant drugs", Pharmazie 52 pp. 627-631 (1997).

Anonym Inn Pharm Techn (2004) vol. 4, pp. 109-111 XP008050337.

Assmann S F Lancet 2000 vol. 355 p. 1064-69.

Baraniuk, James N. et al., "Inhibition of Phosphodiesterase 4 in Allergic Rhinitis", (Review of Schmidt et al., J Allergy Clin Immunol 108: 530-536 (2001)), Clinical Trials Report, pp. 191-193.

Barsig, J. et al., "Protection by the Phosphodiesterase-4 Inhibitor Roflumilast of Mice Against Collagen-induced Arthritis", Poster Presentation, 2001.

(56) References Cited

OTHER PUBLICATIONS

Barsig, J. et al., "The Novel Phosphodiesterase-4 Inhibitor Roflumilast Suppresses TNF-a Production and in Combination with Methotrexate Efficiently Protects Mice Against Collagen-induced Arthritis", Arthritis and Rheumatic Diseases, 2001, Poster Presentation.
Barsig, Johannes et al., "The Novel Phosphodiesterase-4 Inhibitor Roflumilast Suppresses TNF-a Production and Efficiently Protects Mice Against Collagen-Induced Arthritis Alone and in Combination with Methotrexate", Arthritis and Rheumatic Diseases, 2001, vol. 44, No. 9, Suppl. S367, Abstract.
Bauer, et al., "Lehrbuch der Pharmazeutischen Technologie", p. 56, (2003).
Beers_M Merck_Manual_of_Diagnosis_and_Therapy 17th_ Edition 1999 p. 568-569 XP002300786.
Bethke, T. et al., "Roflumilast, a new, orally active, selective PDE4 inhibitor, does not interact with inhaled budesonide", Eur RespirJ, 2001, vol. 18, Suppl. 33, 156s, Abstract.
Bethke, T. et al., "Roflumilast, a New, Orally Active, Selective PDE4 Inhibitor, Does Not Interact with Inhaled Budesonide", Eur Respir J, 2001, Poster Presentation.
Bethke, T. et al "Smoking has no effect on the pharmacokinetics of roflumilast, a new, orally active, selective PDE4 inhibitor", Eur RespirJ, 2001, vol. 18, Suppl. 33, 156s, Abstract.
Bethke, T. et al., "The New PDE4 Inhibitor Roflumilast Does Not Influence Cardiovascular Function", Am J Respir Crit Care Med, 2001, vol. 163, A431, Abstract.
Bredenbroker et al., "Safety of Once-Daily Roflumilast, a New, Orally Active, Selective Phosphodiesterase 4 Inhibitor, in Patients with COPD" (May 2002), poster.
Bredenbroker et al., "Safety of Once-Daily Roflumilast, a New, Orally Active, Selective Phosphodiesterase 4 Inhibitor, in Patients with COPD", Am J Respir Crit Care Med (May 2002), 165, A595.
Brusasco v Thorax 2003 vol. 58, p. 399-404.
Buehler, V., "Kollidon: Polyvinylpyrrolidone for the pharmaceutical industry", 6th Ed., BASF, p. 1-287, (1995).
Bundschuh, D.S. et al., "Anti-inflammatory and Immunomodulatory Potential of Roflumilast, a Novel PDE4 Inhibitor", Am J Respir Crit Care Med, 2001, vol. 163, A431, Abstract.
Bundschuh, D.S. et al., "In vitro and in vivo anti-inflammatory activity of the novel PDE4 inhibitor roflumilast", Eur Respir J, 2001, vol. 18, Suppl. 33, 35s, Abstract.
Bundschuh. D.S. et al.. "In Vitro and in Vivo Anti-Inflammatory Activity of the Novel PDE4 Inhibitor Roflumilast". Eur Respir J. 2001. Poster Presentation.
Calverly P M A Lancet 2009 vol. 374 p. 685-94.
Calverly P M Am J Respir Crit Care Med 2007 vol. 176 p. 154-61.
Calverly P M Eur Respir J 2003 vol. 22 p. 912-19.
Calverly P M Lancet 2003 vol. 362 p. 1053-61.
Calverly P M N Engl J Med 2007 vol. 356 p. 775-89.
Calverly P M Respir Res 2008 vol. 9 p. 73.
Calverly, P., Lancet 2003, vol. 361, pp. 449-456.
Casas J P J Intern Med 2008 vol. 264 p. 295-314.
Chiou W L J Pharm Sci (1971) vol. 60 pp. 1282-1302.
CN Office Action dated Mar. 29, 2009.
Cocci_F Int_J_Biochem_Cell_Biol 2002 vol. 36 No. 6 pp. 594-604.
Croda Japan Kk Crodesta sucrose fatty acid ester.
David, M. et al., "Influence of food intake on the pharmacokinetics of roflumilast, a new, orally active, selective PDE4 inhibitor", Eur RespirJ, 2001, vol. 18, Suppl. 33, 42s, Abstract.
David, M. et al., "Influence of Food Intake on the Pharmacokinetics of Roflumilast, a New, Orally Active, Selective PDE4 Inhibitor", Eur Respir J, 2001, Poster Presentation.
Definition of solution colloidal from Hawleys Chemical Condensed Dictionary 14th edition 2002.
Donaldson G C Thorax 2002 vol. 57 p. 847-52.
Drugs_in_R_and_D 2004 vol. 5 No. 3 p. 176-181 XP008036613.
EC Office Action dated Jul. 31, 2008.

EPO Office Action Dated Nov. 19, 2010 in corresponding EP case citing EP1161950A1.
Exhibit B-5 Handbook of Pharmaceutical Excipients 2nd Ed 1994.
Exhibit B-6 Release controlled Oral Preparation.
Fabbri L M Lancet 2009 vol. 374 p. 695-703.
Fialkov Y., Chemical Abstracts 1983 vol. 98 No. 23 p. 603.
Final Rejection mailed May 7, 2010, which issued in corresponding U.S. Appl. No. 11/501,836.
Fox J Am J Resp Crit Care Med 2003 vol. 167 p. A91.
German E J Eye Lond 1999 Pub Med Result vol. 13 pp. 93-100.
Glenn M R Pharm Tech Europe (1994) pp. 24-35.
Griswold_D Journal_of_Pharmacology_and_Experimental_ Therapeuctics 1998 vol. 287 No. 2 p. 705-711.
Grootendorst D C Thorax 2007 vol. 62 p. 1081-87.
Hafner, Dietrich et al., "Additive Effects of Phosphodiesterase-4 Inhibition on Effects of rSP-C Surfactant", AmJ Respir Crit Care Med, 2000, vol. 161, pp. 1495-1500.
Hahn H., Chemical Abstracts 1963 vol. 58 No. 9.
Hanifin J Journal of Investigative Dermatology (1996) vol. 107, pp. 51-56.
Hauns, B. et al., "Safety-related performance is not impaired by the new PDE-4 inhibitor Roflumilast", Eur Respir J, 2000, vol. 16, Suppl. 31, 277S, Abstract.
Herberg, KW. et al., "Treatment with the New PDE4 Inhibitor Roflumilast Does Not Impair Vigilance and Traffic Safety", Eur J Clin Pharmacol, 2000, vol. 56, No. 2, A29, Abstract.
Hermann R J Clin Pharmacol 2007 vol. 47 p. 1005-1013.
Hilden L R J of Pharma Sciences 2004 p. 3-12 vol. 93.
Hoymann, H.G. et al., "Inhibition by Roflumilast of Airway Hyperresponsiveness to Acetylcholine 48H After Allergen Challenge in Rats", Am J Respir Crit Care Med, 2001, vol. 163, A431, Abstract.
Hoymann, H.G. et al., "Inhibition by Roflumilast of Airway Hyperresponsiveness to Acetylcholine 48 h after Allergen Challenge in Rats", Am J Respir Crit Care Med, 2001, Poster Presentation.
Hunnemeyer, A. et al., "Pharmacokinetics of Roflumilast and its Active Metabolite, Roflumilast-N-Oxide, Is Not Influenced by Smoking", Am J Respir Crit Care Med, 2002, vol. 165, A594, Abstract.
Hunnemeyer, A. et al., "Pharmacokinetics of Roflumilast and its Active Metabolite Roflumilast-N-Oxide Is Not Influenced by Smoking", Am J Respir Crit Care Med, 2002, Poster Presentation.
Izikki, Mohamed et al., "Effects of Roflumilast, a Phosphodiesterase-4 Inhibitor, on Hypoxia- and Monocrotaline-Induced Pulmonary Hypertension in Rats", The Journal of Pharmacology and Experimental Therapeutics, 2009, vol. 330, No. 1, pp. 54-62, The American Society for Pharmacology and Experimental Therapeutics.
JP Office Action dated Sep. 14, 2007.
KAST Pharmaceutics 1998, pp. 361-366.
Kazumasa S., Chemical Abstracts 1988 vol. 108 No. 15 Abstract No. 131583p.
Keipert et al., Pharmazie (1986) vol. 41, pp. 400-404.
Kessler R Chest 2006 vol. 130 p. 133-42.
Kollidone Handbook 4th ed., BASF, 1998.
KR Office Action dated Oct. 7, 2010.
Kumar Rakesh K J Pharmacol Exp Ther 2003 vol. 307 p. 349-355.
Kurashima T Jpn J Allergol (1991), pp. 160-163, vol. 40.
Lahu G J Clin Pharm 2010.
Lanes S F Am J Respir Crit Care Med 2008 vol. 178 p. 543-44.
Leichtl et al., "Efficacy of Once-Daily Roflumilast, A New, Orally Active, Selective Phosphodiesterase 4 Inhibitor, in Chronic Obstructive Pulmonary Disease" (May 2002), poster.
Leichtl et al., "Efficacy of Once-Daily Roflumilast, a New, Orally Active Selective Phosphodiesterase 4 Inhibitor, in Chronic Obstructive Pulmonary Disease", Am J Respir Crit Car Med (May 2002), 165, A229.
Lewis L., J. Microencapsulation vol. 15, No. 5 (1998), pp. 555-567 XP000771706.
MacIntyre_N_R Pharmacotherapy 2004 vol. 24 No. 5 p. 33S-43S XP008036609.
Mahler D A Chest 1984 vol. 85 p. 751-58.

(56) References Cited

OTHER PUBLICATIONS

Martin, Thomas J., "PDE4 inhibitors—A review of the recent patent literature", IDrugs, 2001, vol. 4, No. 3, pp. 312-338, PharmaPress Ltd.
Meyer, H. , "Charackterisierung und Beeinflussung der Losungseigenschaften von 6-Bromcip", Dissertation 1995, p. 154-189, (1995).
Mueller R.H., Pharmazeutische Technologie Moderne Arzneiformen, (1997) pp. 80-91.
Nell, H. et al., "Acute Anti-Inflammatory Effect of the Novel Phosphodiesterase 4 Inhibitor Roflumilast on Allergen Challenge in Asthmatics After a Single Dose", Am J Respir Crit Care Med, 2000, vol. 161, No. 3, Part 2, A200, Abstract.
Non-Final Rejection mailed Aug. 7, 2009, which issued in corresponding U.S. Appl. No. 11/501,836.
Non-Final Rejection mailed Feb. 29, 2012, which issued in corresponding U.S. Appl. No. 12/876,996.
Non-Final Rejection mailed Feb. 29, 2012, which issued in corresponding U.S. Appl. No. 11/501,836.
Non-Final Rejection mailed Jan. 4, 2012, which issued in corresponding U.S. Appl. No. 13/008,842.
Non-Final Rejection mailed Mar. 20, 2009, which issued in corresponding U.S. Appl. No. 11/501,836.
Norman P. Expert Opinion Therapeutic Patents 1999 pp. 1101-1118 vol. 9 No. 8.
Odian G., Wiley Sons, (1991), pp. 19-23.
Office Action dated May 19, 2010 in U.S. Appl. No. 11/342,621.
Office Action dated Aug. 9, 2010 in U.S. Appl. No. 11/342,621.
Office Action dated Jan. 11, 2006 in U.S. Patent No. 7,175,854.
Office Action dated Apr. 20, 2010 in U.S. Appl. No. 12/149,250.
Office Action dated Oct. 22, 2010 in U.S. Appl. No. 12/149,250.
Office Action dated Oct. 9, 2007 in U.S. Appl. No. 10/515,698.
Office Action dated Jan. 23, 2008 in U.S. Appl. No. 10/515,698.
Office Action dated Jul. 24, 2008 in U.S. Appl. No. 10/515,698.
Office Action dated Mar. 13, 2009 in U.S. Appl. No. 10/515,896.
Office Action dated Mar. 26, 2010 in U.S. Appl. No. 10/515,896.
Office Action dated Dec. 20, 2007 in U.S. Appl. No. 11/885,837.
Office Action dated Oct. 14, 2010 in U.S. Appl. No. 11/885,837.
Office Action PH Jun. 16, 2009.
Opposition filed in the name of Hexal AG against EP1478399 of Nycomed GmbH, filed Feb. 20, 2003, granted Mar. 21, 2012.
Pfizer Centre Source Dexamethasone USP Micronized (2010).
Pharmacy, 4th edition, p. 114-117.
Poppe, H. et al., "Effects of a Selective PDE4-Inhibitor AWD 12-281 in Comparison With SB 207499 and Roflumilast on Tracheal Phenol Red Secretion in Mice and LPS-Induced Neutrophilia in BAL in Lewis Rats and Domestic Pigs", Am J Respir Crit Care Med, 2001, vol. 163, No. 5, A, Abstract.
Pruniaux M Am J Resp Crit Care Med 2003 vol. 167 p. A874.
PVP disclosure—downloaded from the internet (Jan. 21, 2008).
Rabe K F A J Respir Crit Care Med 2007 vol. 176 p. 532-55.
Rabe K F Expert Reviews Resp Med 2010 vol. 4 p. 543-555.
Rabe K F Lancet 2005 vol. 366 p. 563-71.
Rabe Lancet 2005 vol. 366 p. 1846-1847.
Rabin R Ann Med 2001 vol. 33 p. 337-43.
Reid_P_T Current_Pharmaceutical_Design 2003 vol. 9 p. 25-38 XP008036607.
Rennard_S Respiratory Research 2011 vol. 18 p. 12.
Response to EPO Communication Pursuant Article 94-3 (2009).
Response to Official Action and data filed Nov. 9, 2009. In corresponding European Patent Application No. 03704652.1-2123, 27 pages.
Rolando M Survey of Ophthalmology (2001), vol. 45, pp. S203-S210.
Safety data sheet CRODESTA F10-HB03671 Sucrose Distearate Croda Europe Ltd (2005).
Safety data sheet CRODESTA F110 HB03722Sucrose Stearate and Sucrose Stearate Croda Europe Ltd (2005).
Safety data sheet CRODESTA F160 HB03750 Sucrose Stearate Croda Europe Ltd (2005).
Safety data sheet CRODESTA F20 HB03668 Sucrose Distearate Croda Europe Ltd (2005).
Safety data sheet CRODESTA F50 HB03669 Sucrose Distearate Croda Europe Ltd (2005).
Safety data sheet CRODESTA SL40 HB03791 Aqua and Sucrose Cocoate and Alcohol Croda Europe Ltd (2005).
Schmidt, Bernhard MW. et al., "The phosphodiesterase 4 inhibitor roflumilast is effective in the treatment of allergic rhinitis", J Allergy Clin Immunol, 2001, vol. 108, No. 4, pp. 530-536, Mosby, Inc.
Sin D D Thorax 2006 vol. 61 p. 1-3.
Snoeck-Stroband J B Eur Respir J 2008 vol. 31 p. 70-77.
Soler-Cataluna JJ Thorax 2005 vol. 60 p. 925-31.
Solutol HS Technical Information Jul. 2003.
Sorbera, L.A. et al., "Roflumilasl: Antialiergy/Antiasthmatic Treatment of COPD Phosphodiesterase 4 Inhibitor", Drugs of the Future, 2000, vol. 25, No. 12, pp. 1261-1264, Prous Science.
Spencer S Am J Respir Crit Care Med 2001 vol. 163 p. 122-128.
Spina D Br J Pharmacol 2008 vol. 155 p. 308-15.
Stebbins K Am J Resp Crit Care Med 2003 vol. 167 p. A486.
Stockley R A Thorax 2006 vol. 61 p. 122-28.
Strickley R G Pharmaceutical Research 2004 vol. 21 2 p. 201-230.
Sucker, H., Pharmazeutische Technologie: Beschrelbung der Arznelformen Spezielle Entwicklung der Dermatika, p. 629-636 and p. 650-665 (1978).
Tashkin D P N Engl J Med 2008 vol. 359 p. 1543-54.
Tenor et al, "Pharmacology, Clinical Efficacy, and Tolerability of Phosphodiesterase-4 Inhibitors: Impact of Human Pharmacokinetics", Handbook of Experimental Pharmacology, (2011) pp. 85-119.
Tenor, "Guidance for Industry, Chronic Obstructive Pulmonary Disease: Developing Drugs for Treatment" (2007) 17 pages.
Thurlbeck_W_M American_Review_Respiratory_Disease 1967 vol. 95 No. 5 p. 752-764 XP008036612.
Timmer, W. et al., "Safety and Efficacy of the New PDE4 Inhibitor Roflumilast Administered to Patients with Exercise-Induced Asthma Over 4 Weeks", Am J Respir Crit Care Med, 2000, vol. 161, No. 3, Part 2, A505, Abstract.
Timmer, W. et al., "The Clinical Efficacy of the New PDE4 Inhibitor Roflumilast in Exercise-Induced Asthma is Accompanied by Suppression of LPS-Stimulated TNF-a Levels", Europ J Clin Pharm, 2000, vol. 56, No. 2, A29, Abstract.
Timmer, W. et al., "Treatment with Therapeutic Doses of the New PDE4Inhibitor Roflumilast Does Not Influence Cardiovascular Function", Europ J Clin Pharm, 2000, vol. 56, No. 2, A29, Abstract.
Toshiro Murata Konando (1997) 5th edition pp. 112-114.
Tros de Ilarduya et al., "Solubilization and Interaction of Sulindac with Polyvinylpyrrolidone K30 in the Solid State and in Aqueous Solution", Drug Development and Industrial Pharmacy, 24(3), 295-300 (1998).
Von Richter O Clin Pharmacokin 2007 vol. 46 p. 613-622.
Washington Ocular drug delivery particulates (2000) pp. 265, 16 pages.
Weimar, C. et al., "No interaction of roflumilast, a new, orally active, selective PDE4 inhibitor, with inhaled salbutamol", Eur RespirJ, 2001, vol. 18, Suppl. 33, 156s, Abstract.
Weimar, C. et al., "No Interaction of Roflumilast, a New, Orally Active, Selective PDE4 Inhibitor, with Inhaled Salbutamol", Eur Respir J, 2001, Poster Presentation.
Wollin, L. et al., "Inhibition by Roflumilast of Airway Hyperresponsiveness to Adenosine and Pulmonary Inflammation in Allergen-challenged Brown Norway Rats", Eur Respir J, 2001, Poster Presentation.
Wollin, L. et al., "Inhibition by Roflumilast of Airway Hyperresponsiveness to Adenosine and Pulmonary Neutrophil Accumulation 3H After Allergen Challenge in Rats", Am J Respir Crit Care Med, 2001, vol. 163, A432, Abstract.
Wollin, L. et al., "Inhibition by roflumilast of airway hyperresponsiveness to adenosine and pulmonary inftammation in allergen challenged Brown-Norway rats", Eur Respir J, 2001, vol. 18, Suppl. 33, 35s, Abstract.
Yagupolskii_L_M Chemical Abstracts 1961 vol. 55 No. 18.
Yliruusi, J. K., et al., "A new Method to evaluate the elastic behavior of tablets during compression", Drug: Oev. Ind. Pharm., vol. 23, No. 1, p. 63-68, (1997), 1 pg.

(56) References Cited

OTHER PUBLICATIONS

Zech et al., "High oral bioavailabiity of roflumilast, a new, orally active once daily PDE4 inhibitor" (2001) 11 pages.
Zech, K. et al., "High oral absolute bioavailability of roflumilast, a new, orally active, once daily PDE4 inhibitor", Eur Respir J, 2001, vol. 18, Suppl. 33, 20s, Abstract.
Zelko, R., et al., "Effects of storage conditions on the free volume of polyvinylpyrrolidone: comparison of positron lifetime data with tensile strength of tablet", Pharm. Res., vol. 17, No. 8, p. 1030-1032, (2000), 2 pg.
Declaration of Walter Palosch under Rule 1.132 dated Mar. 13, 2013 in U.S. Appl. No. 13/547,945, filed Jul. 12, 2012, 4 pages.
Declaration of Dirk Bredenbroeker under Rule 1.132 dated Aug. 17, 2012 in U.S. Appl. No. 11/501,836, filed Aug. 10, 2006, 7 pages.
Declaration of Hermann Tenor under Rule 1.132 dated Aug. 16, 2012 in U.S. Appl. No. 11/501,836, filed Aug. 10, 2006, 9 pages.
Declaration of Hermann Tenor under Rule 1.132 date Nov. 9, 2012 in U.S. Appl. No. 12/876,996, filed Sep. 7, 2010, 3 pages.
Declaration of Hartmut Ney under Rule 1.132 dated Apr. 19, 2007 in U.S. Appl. No. 10/505,138, filed Aug. 19, 2004, 25 pages.
Declaration of Karl Zech under Rule 1.132 dated Jan. 24, 2013 in U.S. Appl. No. 12/876,996, filed Sep. 7, 2010, 4 pages.
Sin et al., "Skeletal muscle weakness, reduced exercise tolerance, and COPD: is systemic inflammation the missing link?", Thorax, 2006, 61:1-3.
Applicant Appeal Brief filed in U.S. Appl. No. 12/149,250, filed Mar. 21, 2011, 20 pages.
Applicant Appeal Brief filed in U.S. Appl. No. 10/515,896, filed Jan. 26, 2011, 37 pages.
Applicant Appeal Brief filed in U.S. Appl. No. 11/662,887, filed Feb. 2, 2012, 33 pages.
Applicant Appeal Brief filed in U.S. Appl. No. 10/505,138, filed Mar. 30, 2009, 40 pages.
Applicant Reply Brief filed in U.S. Appl. No. 10/515,896, dated Jun. 13, 2011, 26 pages.
Applicant Reply Brief filed in U.S. Appl. No. 11/662,887, filed May 30, 2012, 13 pages.
Applicant Reply Brief filed in U.S. Appl. No. 10/515,698, filed Mar. 29, 2010, 11 pages.
Applicant Reply Brief filed in U.S. Appl. No. 10/505,138, filed Aug. 3, 2009, 37 pages.
Applicant Appeal Briefs filed in U.S. Appl. No. 10/515,698, filed Aug. 26, 2009 and Oct. 26, 2009, 34 pages.
USPTO Non-final Office Action issued in U.S. Appl. No. 11/642,621, dated May 19, 2010, 14 pages.
USPTO Non-final Office Action dated Sep. 14, 2010, in U.S. Appl. No. 11/885,837, 13 pages.
USPTO Final Office Action dated Oct. 27, 2010 in U.S. Appl. No. 12/149,250, 8 pages.
USPTO Final Office Action dated Aug. 19, 2008 in U.S. Appl. No. 10/515,698, 9 pages.
USPTO Patent Board Decision issued in U.S. Appl. No. 10/505,138, dated Oct. 20, 2010, 19 pages.
USPTO Examiner's Answer to Appeal Brief issued in U.S. Appl. No. 10/505,138, dated Jun. 2, 2009, 19 pages.
USPTO Final Office Action issued in U.S. Appl. No. 11/642,621, dated Nov. 1, 2010, 8 pages.
USPTO Notice of Allowance issued in U.S. Appl. No. 11/642,621, dated Jan. 24, 2011, 6 pages.
USPTO Restriction Requirement in U.S. Appl. No. 11/642,621, dated May 15, 2009, 9 pages.
USPTO Final Office Action issued in U.S. Appl. No. 10/433,398, dated Jul. 3, 2006, 9 pages.
USPTO Notice of Allowance issued in U.S. Appl. No. 10/433,398, dated Sep. 21, 2006, 5 pages.
USPTO Final Office Action issued in U.S. Appl. No. 10/515,698, dated Jan. 16, 2009, 7 pages.
USPTO Examiner's Answer to Appeal Brief issued in U.S. Appl. No. 10/515,698, dated Feb. 2, 2010, 11 pages.
USPTO Patent Board Decision issued in U.S. Appl. No. 10/515,698, dated Jun. 27, 2011, 8 pages.
USPTO Non-final Office Action issued in U.S. Appl. No. 13/219,056, dated Oct. 19, 2011, 18 pages.
USPTO Final Office Action issued in U.S. Appl. No. 13/219,056, dated Apr. 25, 2012, 10 pages.
USPTO Examiner's Answer to Appeal Brief issued in U.S. Appl. No. 12/149,250, dated Jun. 8, 2011, 10 pages.
USPTO Non-final Office Action issued in U.S. Appl. No. 10/515,896, dated Jun. 23, 2009, 17 pages.
USPTO Non-final Office Action issued in U.S. Appl. No. 10/515,896, dated Sep. 14, 2010, 26 pages.
USPTO Examiner's Answer to Appeal Brief issued in U.S. Appl. No. 10/515,896, dated Apr. 14, 2011, 31 pages.
USPTO Patent Board Decision issued in U.S. Appl. No. 10/515,896, dated Jun. 13, 2013, 18 pages.
USPTO Non-final Office Action issued in U.S. Appl. No. 11/662,887, dated Jun. 28, 2010, 18 pages.
USPTO Non-final Office Action issued in U.S. Appl. No. 11/662,887, dated Dec. 16, 2010, 16 pages.
USPTO Final Office Action issued in U.S. Appl. No. 11/662,887, dated Jun. 8, 2011, 12 pages.
USPTO Examiner's Answer to Appeal Brief issued in U.S. Appl. No. 11/662,887, dated Mar. 30, 2012, 19 pages.
USPTO Restriction Requirement issued in U.S. Appl. No. 11/662,888, dated Sep. 15, 2008, 8 pages.
USPTO Restriction Requirement issued in U.S. Appl. No. 11/885,837, dated Jun. 8, 2010, 9 pages.
USPTO Final Office Action issued in U.S. Appl. No. 11/885,837, dated Mar. 21, 2011, 11 pages.
USPTO Non-final Office Action issued in U.S. Appl. No. 11/885,837, dated May 23, 2013, 9 pages.
USPTO Notice of Allowance issued in U.S. Appl. No. 13/547,945, dated May 2, 2013, 40 pages.
USPTO Non-Final Office Action issued in U.S. Appl. No. 13/860,264, dated Jun. 12, 2013, 31 pages.
USPTO Notice of Allowance issued in U.S. Appl. No. 13/008,842, dated Jan. 28, 2013, 5 pages.
Exhibit B-6, "Release controlled Oral Preparation," Sep. 2002, 3 pages.
*Pharmacy*, 4th ed., The Peoples Medical Publishing House, edited by Bi Dianzhou, Dec. 2000, 3 pages.
Bethke et al., "Smoking has no effect on the pharmacokinetics of Roflumilast—A New, Orally Active, Selective PDE4 Inhibitor," *Eur Resp J.*, Poster Presentation, 2001, 1 page.

PROCESS FOR THE PREPARATION OF ROFLUMILAST

This application is a continuation application of U.S. Ser. No. 13/547,945 filed on Jul. 12, 2012, which in turn is a continuation of U.S. Ser. No. 12/292,795 filed on Nov. 26, 2008, which in turn is a continuation of U.S. Ser. No. 10/531,720 filed on Apr. 18, 2005 now U.S. Pat. No. 7,470,791 issued on Dec. 30, 2008, which was filed under 35 U.S.C. 371 as a national stage of PCT/EP2004/050272 filed on Mar. 8, 2004, which clams priority of EP Application No. 03005245.0 filed Mar. 10, 2003.

TECHNICAL FIELD

The present invention relates to a novel, improved process for the preparation of N-(3,5-dichloropyrid-4-yl)-3-cyclopropylmethoxy-4-difluoromethoxybenzamide (INN: roflumilast).

PRIOR ART

The international patent application WO 95/01338 describes the preparation of dialkoxy-substituted benzamides, including roflumilast, and the use thereof as PDE4 inhibitors. The international applications WO 94/02465 and WO 93/25517 also describe the preparation of dialkoxy-substituted benzamides. In the International patent application WO03/070279 oral dosage forms comprising roflumilast are described. In the international patent application WO03/099334 topically applicable pharmaceutical preparations comprising roflumilast are described. Organic Process Research & Development 2, 157-168 (1998) discloses improved processes for the preparation of 3-(cyclopentyloxy)-N-(3,5-dichloropyrid-4-yl)-4-methoxybenzamide (INN: piclamilast).

In the international applications WO 94/02465 and WO 93/25517, the dialkoxy-substituted benzamides are obtained by reacting activated benzoic acid derivatives of the general formula

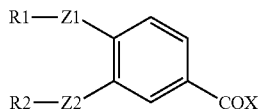

with amines of the general formula R3NH$_2$. Activated benzoic acid derivatives mentioned are acid halides, especially acid chlorides or else anhydrides. The reaction may take place in the presence of a base, e.g. of an organic base such as, for example, triethylamine, in the presence of a cyclic base such as, for example, N-methylmorpholine or pyridine or else in the presence of an alkali metal hydride such as, for example, sodium hydride, in an inert solvent such as, for example, tetrahydrofuran, dimethylformamide or dichloromethane.

3-(Cyclopentyloxy)-N-(3,5-dichloropyrid-4-yl)-4-methoxybenzamide (INN: piclamilast) is obtained in WO 93/25517 by reacting 3-cyclopentyl-4-methoxybenzoic acid, which has been deprotonated with N-methylmorpholine, with 4-amino-3,5-dichloropyridine in tetrahydrofuran. In WO 94/02465, 3-(cyclopentyloxy)-N-(3,5-dichloropyrid-4-yl)-4-methoxybenzamide (INN: piclamilast) is prepared by mixing together and subsequently melting 4-amino-3,5-dichloropyridine and 3-cyclopentyloxy-4-methoxybenzoyl chloride.

In the process for preparing roflumilast described in WO 95/01338, a solution of 0.0275 mol of 3-cyclopropylmethoxy-4-difluoromethoxybenzoyl chloride in tetrahydrofuran is added dropwise to a suspension of 0.03 mol of 4-amino-3,5-dichloropyridine and 0.066 mol of NaH (in mineral oil) in tetrahydrofuran at 15-20° C.

In the improved process described in Organic Process Research & Development 2, 157-168 (1998) for preparing 3-(cyclopentyloxy)-N-(3,5-dichloropyrid-4-yl)-4-methoxybenzamide (INN: piclamilast), firstly 0.218 mol of KOtBu is added to 0.22 mol of 4-amino-3,5-dichloropyridine at 90° C., and then a solution of 0.2 mol of 3-cyclopentyloxy-4-methoxybenzoyl chloride is added. The mixture is boiled under reflux for some time, cooled to 90° C. again and then a further 0.218 mol of KOtBu is added. This is followed by boiling under reflux again, before the reaction mixture is worked up by methods known to the skilled person.

None of the processes described in the international applications WO 93/25517 and WO 94/02465 for preparing piclamilast, nor the process described in WO 95/01338 for preparing roflumilast, appear to be suitable for the industrial preparation of roflumilast of high purity.

Although the improved process described in Organic Process Research & Development 2, 157-168 (1998) for preparing 3-(cyclopentyloxy)-N-(3,5-dichloropyrid-4-yl)-4-methoxybenzamide (INN: piclamilast) has already been optimized for feasibility on the industrial scale, when applied analogously to roflumilast it leads to the formation of more than 3% by weight of the by-product N-(3,5-dichloropyrid-4-yl)-3-cyclopropylmethoxy-4-hydroxybenzamide, which cannot be reduced even by multiple recrystallization.

DESCRIPTION OF THE INVENTION

It has now been found, surprisingly, that the formation of by-products, especially of the abovementioned by-product, can be very substantially averted when an activated derivative of 3-cyclopropylmethoxy-4-difluoromethoxybenzoic acid is reacted with an excess of the anion of 4-amino-3,5-dichloropyridine.

A first aspect of the invention is therefore a process for the preparation of roflumilast by reacting the anion of 4-amino-3,5-dichloropyridine (1)

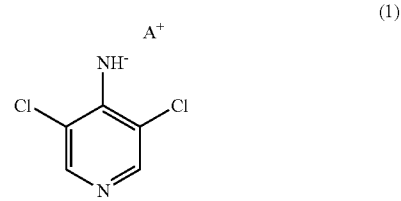

with an activated derivative of 3-cyclopropylmethoxy-4-difluoromethoxybenzoic acid (2),

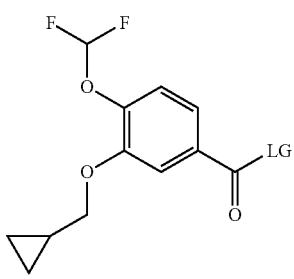

(2)

characterized in that the molar ratio of the employed anion of #amino-3,5-dichloropyridine to the activated derivative of 3-cyclopropylmethoxy-4-difluoromethoxybenzoic acid is at least 1.5 and at most 3, preferably at least 1.8 and at most 2.7, particularly preferably at least 2 and at most 2.5 and very particularly preferably 2.2.

$A^+$ in the formula 1 is a cation; $A^+$ is, for example, an alkali metal cation, preferably the potassium cation. LG in formula 2 is a suitable leaving group, preferably a chlorine atom, a bromine atom or a radical of the formula OC(O)-1-4C-alkyl. LG is particularly preferably a chlorine atom.

1-4C-alkyl in the formula OC(O)-1-4C-alkyl is a straight-chain or branched alkyl radicals having 1 to 4 carbon atoms. Examples which may be mentioned are the butyl, isobutyl, sec-butyl, tert-butyl, propyl, isopropyl, ethyl and methyl radicals.

Reaction of the anion of 4-amino-3,5-dichloropyridine (1) with an activated derivative of 3-cyclopropylmethoxy-4-difluoromethoxybenzoic acid (2) can be carried out in all conventional inert solvents such as, for example, dichloromethane, toluene, xylene, dimethylformamide or N-methylpyrrolidone. The use of dimethylformamide or N-methylpyrrolidone is preferred. The use of dimethylformamide is very particularly preferred.

A further aspect of the invention is therefore one of the processes described above for preparing roflumilast, characterized in that reaction of the anion of 4-amino-3,5-dichloropyridine (1) with an activated derivative of 3-cyclopropylmethoxy-4-difluoromethoxybenzoic acid (2) is carried out in a solvent selected from the group of dichloromethane, toluene, xylene, dimethylformamide or N-methylpyrrolidone, preferably in dimethylformamide or N-ethylpyrrolidone and very preferably in dimethylformamide.

The reaction temperatures for the conversion are between 0° C. and the boiling point of the solvent used. The conversion is preferably carried out at temperatures between 15 and 40° C., very particularly preferably between 20 and 30° C.

A further aspect of the invention is therefore one of the processes described above for preparing roflumilast, characterized in that reaction of the anion of 4-amino-3,5-dichloropyridine (1) with an activated derivative of 3-cyclopropylmethoxy-4-difluoromethoxybenzoic acid (2) is carried out at a temperature between 0° C. and the boiling point of the inert solvent used, preferably at a temperature between 15 and 40° C. and particularly preferably at a temperature between 20 and 30° C.

In the reaction of the anion of 4-amino-3,5-dichloropyridine (1) with an activated derivative of 3-cyclopropylmethoxy-4-difluoromethoxybenzoic acid (2) it is possible to add either the anion of 4-amino-3,5-dichloropyridine (1) or the activated derivative of 3-cyclopropylmethoxy-4-difluoromethoxybenzoic acid (2) to the respective other reactant. However, the process in which the activated derivative of 3-cyclopropylmethoxy-4-difluoromethoxybenzoic acid is added as second reactant to the anion of 4-amino-3,5-dichloropyridine (1) is preferred.

Activated derivatives of 3-cyclopropylmethoxy-4-difluoromethoxybenzoic acid (2) may be, for example, the corresponding acid halides, especially the acid chloride or else an anhydride [LG then corresponds to Cl, Br or OC(O)-1-4C-alkyl]. The acid halides are preferred in this connection, and the acid chloride is very particularly preferred.

A further aspect of the invention is therefore the process described above for preparing roflumilast, characterized in that the activated derivative of 3-cyclopropylmethoxy-4-difluoromethoxybenzoic acid is a 3-cyclopropylmethoxy-4-difluoromethoxybenzoyl halide, especially 3-cyclopropylmethoxy-4-difluoromethoxybenzoyl chloride.

Strong bases selected from the group of KOtBu, NaOtBu and LiOtBu are particularly suitable for preparing the anion of 4-amino-3,5-dichloropyridine. The use of KOtBu is preferred.

A further aspect of the invention is therefore one of the processes described above for preparing roflumilast, characterized in that a base selected from the group of KOtBu, NaOtBu or LiOtBu is used to prepare the anion of 4-amino-3,5-dichloropyridine. KOtBu is preferably used.

The molar ratio of employed base to 4-amino-3,5-dichloropyridine is in this case advantageously in the range from 0.8 to 1.1 and preferably in the range from 0.9 to 1.0.

A further aspect of the invention is therefore one of the processes described above for preparing roflumilast, characterized in that the molar ratio of employed base to 4-amino-3,5-dichloropyridine in the anion formation is between 0.8 and 1.1, preferably between 0.9 and 1.0.

The activated derivative of 3-cyclopropylmethoxy-4-difluoromethoxybenzoic acid is prepared by methods known to the skilled person.

The corresponding acid chloride is, for example, preferably prepared by reacting 3-cyclopropylmethoxy-4-difluoromethoxybenzoic acid with thionyl chloride in the presence of catalytic amounts of dimethylformamide in an inert solvent. An example of an inert solvent is toluene or xylene; the chlorination reaction is typically carried out at 70 to 90° C.

The roflumilast prepared by the processes described above is distinguished by a purity of a 99% by weight. Crystallization from isopropanol/water (ratio:between 85:1.5 and 100:0% by volume, preferably between 90:10 and 95:5% by volume) allows the purity to be increased further to ≥99.8% by weight.

A further aspect of the invention is therefore one of the processes described above for preparing roflumilast, characterized in that the product resulting from the process is recrystallized in a mixture of isopropanol and water (ratio isopropanol/water:between 85:15 and 100:0% by volume, preferably between 90:10 and 95:5% by volume).

Further aspects of the invention which should be mentioned are:

Roflumilast prepared by one of the processes described above, characterized in that its purity is a 99% by weight, preferably a 99.8% by weight.

Roflumilast prepared by one of the processes described above, characterized in that it contains less than 0.1% by weight, preferably 0.05% by weight, of the by-product N-(3,5-dichloropyrid-4-yl)-3-cyclopropylmethoxy-4-hydroxybenzamide.

The processes according to the invention for the preparation of roflumilast are in particular useful for the large-scale preparation of roflumilast; high-purity roflumilast can be prepared in a scale of about 5 to 500 kg per batch.

Roflumilast prepared by one of the processes described above can be used in human and veterinary medicine for the treatment and prophylaxis, for example, of the following diseases: acute and chronic (especially inflammatory and allergen-induced) airway disorders of various etiologies (bronchitis, allergic bronchitis, bronchial asthma, emphysema, COPD); dermatoses (especially of a proliferative, inflammatory and allergic nature) such as, for example, psoriasis (vulgaris), toxic and allergic contact eczema, atopic eczema, seborrhoic eczema, lichen simplex, sunburn, pruritus in the genitoanal region, alopecia greata, hypertrophic scars, discoid lupus erythematosus, follicular and extensive pyodermas, endogenous and exogenous acne, acne rosacea and other proliferative, inflammatory and allergic skin disorders; disorders based on excessive release of TNF an leukotrienes, e.g. disorders of the arthritic type (rheumatoid arthritis, rheumatoid spondylitis, osteoarthritis and other arthritic states), disorders of the immune system (AIDS, multiple sclerosis), types of shock [septic shock, endotoxin shock, gram-negative sepsis, toxic shock syndrome and ARDS (adult respiratory distress syndrome)] and generalized inflammations in the gastrointestinal region (Crohn's disease and ulcerative colitis); disorders based on allergic and/or chronic abnormal immunological reactions in the region of the upper airways (pharyngeal space, nose) and adjacent regions (paranasal sinuses, eyes), such as, for example, allergic rhinitis/sinusitis, chronic rhinitis/sinusitis, allergic conjunctivitis and nasal polyps; but also cardiac disorders which can be treated by PDE inhibitors, such as, for example, heart failure, or disorders which can be treated owing to the tissue-relaxant effect of PDE inhibitors, such as, for example, erectile dysfunction or colic of the kidneys and ureters connected with kidney stones; or else disorders of the CNS such as, for example, depressions or arteriosclerotic dementia.

The invention therefore further relates to roflumilast prepared by one of the processes described above for use in the treatment and/or prophylaxis of diseases, especially the diseases mentioned.

The invention also relates to the use of roflumilast prepared by one of the processes described above for the production of pharmaceutical compositions which are employed for the treatment and/or prophylaxis of the diseases mentioned. The disease is preferably an acute or chronic airway disorder (for example asthma, bronchitis, allergic rhinitis, emphysema and COPD), a dermatosis or an arthritic disorder (for example rheumatoid arthritis, rheumatoid spondylitis and osteoarthritis).

The invention furthermore relates to a method for the treatment of mammals, including humans, suffering from one of the mentioned diseases. The method is characterized in that a therapeutically effective amount of roflumilast prepared by one of the processes described above is administered together with conventional auxiliaries and/or excipients to the mammal with the disease. Preferably the disease is an acute or chronic airway disorder (for example asthma, bronchitis, allergic rhinitis, emphysema and COPD), a dermatosis or an arthritic disorder (for example rheumatoid arthritis, rheumatoid spondylitis and osteoarthritis).

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

The pharmaceutical compositions are prepared by processes, which are known per se and familiar to the person skilled in the art. As pharmaceutical composition, the roflumilast prepared according to one of the above-mentioned processes is either employed as such, or preferably in combination with suitable pharmaceutical auxiliaries and/or excipients, e.g. in the form of tablets, coated tablets, capsules, caplets, suppositories, emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved. In the international patent application WO03/070279 oral dosage forms comprising roflumilast are described.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

For the treatment of disorders of the respiratory tract, the roflumilast prepared according to one of the above-mentioned processes is preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the roflumilast prepared according to one of the above-mentioned processes is in particular administered in the form of those pharmaceutical compositions, which are suitable for topical application. For the production of the pharmaceutical compositions, the roflumilast prepared according to one of the above-mentioned processes is preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions. In the international patent application WO03/099334 topically applicable pharmaceutical preparations comprising roflumilast are described.

The dosage of the roflumilast prepared according to one of the above-mentioned processes is in the order of magnitude customary for PDE inhibitors, it being possible to administer the daily dose in one or more dosage units. Customary dosages are disclosed for example in WO95/01338. In general, oral dosage forms contain from 0.01 mg to 5 mg, preferably from 0.05 mg to 2.5 mg, particularly preferably 0.1 mg to 0.5 mg of roflumilast per dosage unit. Dosage forms for topical administration contain from 0.005 mg to 5 mg, preferably 0.01 mg to 2.5 mg particularly preferably 0.1 mg to 0.5 mg of roflumilast per dosage unit. Typically, pharmaceutical compositions of the invention contain 0.01 mg, 0.1 mg, 0.125 mg, 0.25 mg or 0.5 mg of roflumilast per dosage unit.

The following examples serve to illustrate the invention further without restricting it.

Synthesis of Roflumilast

Coupling Step

The potassium salt suspension of the anion of 4-amino-3,5-dichloropyridine in DMF (2-25 equivalents) is introduced into a reaction vessel. A solution of 3-cyclopropylmethoxy-4-difluoromethoxybenzoyl chloride (1 equivalent) in DMF is slowly added to this suspension while stirring vigorously at a temperature of 15 to 40° C., preferably 20 to 30° C. After the reaction is complete, water is slowly added while stirring at 15-25° C., and the pH is adjusted to 2-3 with hydrochloric acid.

The solid is centrifuged or filtered, washed with water, resuspended in a sodium hydroxide solution (pH=9-10), centrifuged or filtered again and washed with water. This moist crude material is, if desired, subjected to a recrystallization from an isopropanol/water mixture (ratio between 85:15 and 100:0, preferably 95:5% by volume). The resulting product is centrifuged or filtered and dried in vacuo at a temperature not exceeding 60° C.

Synthesis of
3-Cyclopropylmethoxy-4-Difluoromethoxybenzoyl Chloride

A reaction vessel is charged with toluene, a catalytic amount of DMF (1-5% by weight of the amount of thionyl chloride employed) and 1 equivalent of 3-cyclopropylmethoxy-4-difluoromethoxybenzoic acid. While stirring, 1 to 4 equivalents of thionyl chloride are slowly added at 70 to 90° C.

After the reaction is complete, the reaction mixture is concentrated in vacuo at 45 to 60° C., and the solvent toluene is replaced by DMF; the resulting 3-cyclopropylmethoxy-4-difluoromethoxybenzoyl chloride solution is used without further purification in the subsequent coupling step.

Synthesis of the Potassium Salt of
4-Amino-3,5-Dichloropyridine

A reaction vessel is charged with DMF and 4-amino-3,5-dichloropyridine (1 equivalent). While stirring vigorously, potassium tert-butoxide (0.8-1.1, preferably 0.9-1.0 equivalent) is added in portions, at a temperature between 15 and 30° C. A suspension of the potassium salt of the anion of 4-amino-3,5-dichloropyridine is obtained and is employed without further purification for the subsequent coupling step.

Process A: Standard process as described above; synthesis of the potassium salt of 4-amino-3,5-dichloropyridine using 1 equivalent of 4-amino-3,5-dichloropyridine and 1 equivalent of potassium tert-butoxide.

Process B: Differing from process A in that the potassium salt of 4-amino-3,5-dichloropyridine is prepared using 1 equivalent of 4-amino-3,5-dichloropyridine and 0.91 equivalent of potassium tert-butoxide.

Process C: Differing from the standard process in that N-methylpyrrolidone is used as solvent instead of DMF in the coupling step and in the preparation of the potassium salt of 4-amino-3,5-dichloropyridine.

Process D: Differing from the standard process in that only 1.8 equivalents, instead of 2-2.5 equivalents, of the potassium salt of 4-amino-3,5-dichloropyridine are employed in the coupling step.

Process E: Differing from the standard process in that 2.7 equivalents, instead of 2-2.5 equivalents, of the potassium salt of 4-amino-3,5-dichloropyridine are employed in the coupling step.

Process F: Differing from the standard process in that the potassium salt of 4-amino-3,5-dichloropyridine is prepared using 1 equivalent of 4-amino-3,5-dichloropyridine and 1.83 equivalents of potassium tert-butoxide.

Process G: The improved process described in Organic Process Research & Development 2, 157-168 (1998) for preparing piclamilast (coupling step) is applied analogously to the preparation of roflumilast.

| Process | Purity after recrystallization from isopropanol/water (data in % by weight) | Content of by-product N-(3,5-dichloropyrld-4-yl)-3-cyclopropylmethoxy-4-hydroxy-benzamide (data in % by weight) |
|---------|---|---|
| A | ≥99.8 | <0.05 |
| B | ≥99.8 | <0.05 |
| C | ≥99.8 | <0.05 |
| D | ≥99.8 | <0.05 |
| E | ≥99.8 | <0.05 |
| F | 96.2 | 0.8 |
| G | 95.4 | 3.47 |

The invention claimed is:

1. A method for the treatment of an acute or chronic airway disorder comprising: administering to a patient suffering from an acute or chronic airway disorder, a therapeutically effective amount of roflumilast having a purity of greater than or equal to 99% by weight, and N-(3,5-dichloropyrid-4-yl)-3-cyclopropylmethoxy-4-hydroxybenzamide present (relative to roflumilast) in an amount greater than zero and less than 0.1% by weight.

2. The method of claim 1, wherein said roflumilast has a purity of greater than or equal to 99.8% by weight.

3. The method of claim 1, wherein said N-(3,5-dichloropyrid-4-yl)-3-cyclopropylmethoxy-4-hydroxybenzamide is present (relative to roflumilast) in an amount greater than zero and less than 0.05% by weight.

4. A method for the treatment of an acute or chronic airway disorder comprising: administering to a patient suffering from an acute or chronic airway disorder, a therapeutically effective amount of a pharmaceutical composition, comprising: roflumilast having a purity of greater than or equal to 99% by weight; N-(3,5-dichloropyrid-4-yl)-3-cyclopropylmethoxy-4-hydroxybenzamide present (relative to roflumilast) in an amount greater than zero and less than 0.1% by weight; and pharmaceutically acceptable auxiliaries and/or excipients.

5. The method of claim 4, wherein said roflumilast has a purity of greater than or equal to 99.8% by weight.

6. The method of claim 4, wherein said N-(3,5-dichloropyrid-4-yl)-3-cyclopropylmethoxy-4-hydroxybenzamide is present (relative to roflumilast) in an amount greater than zero and less than 0.05% by weight.

7. A method for the treatment of an acute or chronic airway disorder comprising: administering to a patient suffering from an acute or chronic airway disorder, a therapeutically effective amount of a pharmaceutical dosage form, comprising: roflumilast having a purity of greater than or equal to 99% by weight; N-(3,5-dichloropyrid-4-yl)-3-cyclopropylmethoxy-4-hydroxybenzamide present (relative to roflumilast) in an amount greater than zero and less than 0.1% by weight; and pharmaceutically acceptable auxiliaries and/or excipients.

8. The method of claim 7, wherein said roflumilast has a purity of greater than or equal to 99.8% by weight.

9. The method of claim 7, wherein said N-(3,5-dichloropyrid-4-yl)-3-cyclopropylmethoxy-4-hydroxybenzamide is present (relative to roflumilast) in an amount greater than zero and less than 0.05% by weight.

10. The method of claim 7, wherein said pharmaceutical dosage form is selected from the group consisting of tablets, coated tablets, capsules, caplets, suppositories, emulsions, suspensions, gels and solutions.

11. The method of claim 7, wherein said pharmaceutical dosage form includes from between 0.1% and 95% roflumilast.

12. The method of claim 7, wherein the pharmaceutical dosage form is an oral dosage form.

13. The method of claim 7, wherein the pharmaceutical dosage form contains from 0.05 mg to 2.5 mg of roflumilast.

14. The method of claim 13, wherein the pharmaceutical dosage form contains from 0.1 to 0.5 mg of roflumilast.

15. The method of claim 14, wherein the pharmaceutical dosage form contains 0.25 mg of roflumilast.

16. The method of claim 14, wherein the pharmaceutical dosage form contains 0.5 mg of roflumilast.

17. A method for the treatment of an acute or chronic airway disorder comprising: administering to a patient suffering from an acute or chronic airway disorder, a therapeutically effective amount of a pharmaceutical tablet, comprising: 0.5 mg of roflumilast having a purity of greater than or equal to 99% by weight; N-(3,5-dichloropyrid-4-yl)-3-cyclopropylmethoxy-4-hydroxybenzamide present (relative to roflumilast) in an amount less than 0.1% by weight; and pharmaceutically acceptable auxiliaries and/or excipients.

18. The method of claim 17, wherein said roflumilast has a purity of greater than or equal to 99.8% by weight.

19. The method of claim 17, wherein said N-(3,5-dichloropyrid-4-yl)-3-cyclopropylmethoxy-4-hydroxybenzamide is present (relative to roflumilast) in an amount greater than zero and less than 0.05% by weight.

20. The method of claim 1, wherein said disorder is selected from the group consisting of asthma, bronchitis, allergic rhinitis, emphysema and chronic obstructive pulmonary disease.

21. The method of claim 4, wherein said disorder is selected from the group consisting of asthma, bronchitis, allergic rhinitis, emphysema and chronic obstructive pulmonary disease.

22. The method of claim 7, wherein said disorder is selected from the group consisting of asthma, bronchitis, allergic rhinitis, emphysema and chronic obstructive pulmonary disease.

23. The method of claim 17, wherein said disorder is selected from the group consisting of asthma, bronchitis, allergic rhinitis, emphysema and chronic obstructive pulmonary disease.

* * * * *

UNITED STATES PATENT AND TRADEMARK OFFICE
CERTIFICATE OF CORRECTION

PATENT NO.         : 8,604,064 B2
APPLICATION NO.    : 13/860248
DATED              : December 10, 2013
INVENTOR(S)        : Bernhard Kohl, Bernd Mueller and Walter Palosch It is certified that error appears in the above-identified patent and that said Letters Patent is hereby corrected as shown below:

On Title Page 3, Item (56), Column 2, Line 1, delete "eficacy" and insert -- efficacy --, therefor.

On Title Page 3, Item (56), Column 2, Line 4, delete "o" and insert -- of --, therefor.

On Title Page 4, Item (56), Column 1, Line 11, delete "tiral" and insert -- trial --, therefor.

On Title Page 4, Item (56), Column 1, Line 17, delete "pateints" and insert -- patients --, therefor.

On Title Page 4, Item (56), Column 1, Line 35, delete "desease," and insert -- disease, --, therefor.

On Title Page 4, Item (56), Column 2, Line 71, delete "Roftumilast" and insert -- Roflumilast --, therefor.

On Title Page 5, Item (56), Column 1, Line 15, delete ""Roftumilast," and insert -- "Roflumilast, --, therefor.

On Title Page 5, Item (56), Column 1, Line 18, delete ""Roftumilast," and insert -- "Roflumilast, --, therefor.

On Title Page 5, Item (56), Column 1, Line 22, delete "roftumilast," and insert -- roflumilast, --, therefor.

On Title Page 5, Item (56), Column 1, Line 24, delete "Roftumilast," and insert -- Roflumilast, --, therefor.

On Title Page 5, Item (56), Column 1, Line 25, delete "Inftuence" and insert -- Influence --, therefor.

On Title Page 5, Item (56), Column 1, Line 37, delete "Roftumilast," and insert -- Roflumilast, --, therefor.

Signed and Sealed this
Sixth Day of May, 2014

Michelle K. Lee
*Deputy Director of the United States Patent and Trademark Office*

On Title Page 5, Item (56), Column 1, Line 40, delete "roftumilast"," and insert -- roflumilast", --, therefor.

On Title Page 5, Item (56), Column 2, Line 22, delete "Roftumilast"," and insert -- Roflumilast", --, therefor.

On Title Page 5, Item (56), Column 2, Line 25, delete "Roftumilast" and insert -- Roflumilast --, therefor.

On Title Page 5, Item (56), Column 2, Line 29, delete "Roftumilast," and insert -- "Roflumilast --, therefor.

On Title Page 5, Item (56), Column 2, Line 32, delete "Roftumilast" and insert -- Roflumilast --, therefor.

On Title Page 5, Item (56), Column 2, Line 35, delete "Roftumilast" and insert -- Roflumilast --, therefor.

On Title Page 5, Item (56), Column 2, Line 36, delete "Roftumilast" and insert -- Roflumilast --, therefor.

On Title Page 5, Item (56), Column 2, Line 39, delete "Roftumilast" and insert -- Roflumilast --, therefor.

On Title Page 5, Item (56), Column 2, Line 42, delete "Roftumilast," and insert -- Roflumilast, --, therefor.

On Title Page 6, Item (56), Column 1, Line 3, delete "LId." and insert -- Ltd. --, therefor.

On Title Page 6, Item (56), Column 1, Line 10, delete "Roftumilast" and insert -- Roflumilast --, therefor.

On Title Page 6, Item (56), Column 2, Line 8, delete "roftumilast," and insert -- roflumilast --, therefor.

On Title Page 6, Item (56), Column 2, Line 14, delete "Roftumilasl:" and insert -- Roflumilast: --, therefor.

On Title Page 6, Item (56), Column 2, Line 14, delete "Antialiergy" and insert -- Antiallergy --, therefor.

On Title Page 6, Item (56), Column 2, Line 34, delete "Roftumilast" and insert -- Roflumilast --, therefor.

CERTIFICATE OF CORRECTION (continued)
U.S. Pat. No. 8,604,064 B2

On Title Page 6, Item (56), Column 2, Line 38, delete "Roftumilast" and insert -- Roflumilast --, therefor.

On Title Page 6, Item (56), Column 2, Line 42, delete "nhibitor" and insert -- Inhibitor --, therefor.

On Title Page 6, Item (56), Column 2, Line 66, delete "roftumilast" and insert -- roflumilast --, therefor.

On Title Page 6, Item (56), Column 2, Line 67, delete "inftammation" and insert -- inflammation --, therefor.

On Title Page 7, Item (56), Column 1, Line 1, delete "bioavailabiity" and insert -- bioavailability --, therefor.